United States Patent [19]

Bergfjord et al.

[11] 4,022,956
[45] May 10, 1977

[54] POLYMERS OF BENZANTHRACENE AS ACTIVE MATRIX MATERIALS

[75] Inventors: John Alf Bergfjord, Macedon; Richard William Radler, Marion; Richard Phillip Millonzi, Macedon, all of N.Y.

[73] Assignee: Xerox Corporation, Stamford, Conn.

[22] Filed: Oct. 2, 1974

[21] Appl. No.: 511,133

Related U.S. Application Data

[62] Division of Ser. No. 374,163, June 27, 1973, Pat. No. 3,896,184.

[52] U.S. Cl. .............................. 526/75; 260/669 R; 526/284
[51] Int. Cl.$^2$ ..................................... C08F 112/32
[58] Field of Search ............... 260/93.5 C, 88.2 C, 260/88.2 D, 666 PY, 668 F, 669 R; 526/284, 75

[56] References Cited

UNITED STATES PATENTS

| | | | |
|---|---|---|---|
| 2,496,867 | 2/1950 | Flowers | 260/93.5 C |
| 2,496,868 | 2/1950 | Flowers | 260/93.5 C |
| 3,156,676 | 11/1964 | Dekking | 260/666 PY |
| 3,716,595 | 2/1973 | Hall | 260/666 PY |
| 3,764,590 | 10/1973 | Mukoh | 260/93.5 C |
| 3,865,798 | 2/1975 | Radler | 260/93.5 C |

*Primary Examiner*—Paul R. Michl
*Attorney, Agent, or Firm*—James J. Ralabate; James P. O'Sullivan; John E. Crowe

[57] ABSTRACT

Vinyl polycyclic aromatics, particularly polycyclics having 3 or more nuclei and their polymers utilizable as active matrix material for xerographic purposes are obtained in high yield by initial conversion of the polycyclic reactant to the aldehyde in the presence of a haloalkyl ether as a formulating agent in the presence of a Friedl-Crafts type catalyst. The aldehyde intermediate is then converted to the vinyl monomer by using a Wittig-type reaction and, thereafter, polymerized, as desired, by the use of a cationic mechanism.

6 Claims, No Drawings

POLYMERS OF BENZANTHRACENE AS ACTIVE MATRIX MATERIALS

This is a division of application Ser. No. 374,163, filed June 27, 1973, now U.S. Pat. No. 3,896,189.

This invention relates to a high yield process for obtaining vinyl monomers of polycyclic aromatics such as substituted 1,2-benzanthracene, corresponding polymeric materials and their utilization as unique active matrix materials for xerographic purposes.

BACKGROUND OF THE INVENTION

The formation and development of images on photoconductive materials by electrostatic means is well known. The best known of the commercial process utilizes a latent electrostatic image on an imaging surface by first uniformly electrostatically charging the surface in the dark and then exposing the electrostatically charged surface to a light and shadow image. The light-struck areas of the imaging layer are thus made conductive and the electrostatic charge selectively dissipated in these areas. The latent positive electrostatic image remaining is made visible by development with a finely divided colored electroscopic material known as "toner". This material is preferentially attracted to those areas on the image-bearing surface which have retained an electrostatic charge. After development, the image is permanently affixed to the photoconductor or transferred to some other suitable material such as paper.

Photoconductor layers useful for xerographic purposes (1) may be homogeneous layers of a single material such as vitreous selenium or (2) may be composite layers containing a photoconductor and another material. One type of composite layer used in xerography is illustrated by U.S. Pat. No. 3,121,006 to Middleton and Reynolds, which described a number of binder layers containing finely-divided particles of a photoconductive inorganic compound such as zinc oxide, dispersed in an electrically insulating organic resin binder. In the systems described in Middleton et al, the binder comprises a material which is incapable of transporting the injected charge carriers generated by the photoconductor particles for any significant distance. As a result, the photoconductor particles must be in substantially continuous particle-to-particle contact throughout the layer to permit sufficient charge dissipation is the light-struck areas. The uniform dispersion of photoconductor particles described in Middleton et al, therefore, represents a high volume concentration (i.e. up to about 50 percent or more by volume) of photoconductive particles.

It has also been found, however, that high photoconductor loadings in a binder layer can adversely affect physical continuity and significantly reduce the mechanical properties of a binder layer. High photoconductor loadings, therefore, are often characterized by brittleness and lack of durability. On the other hand, when the photoconductor concentration is substantially reduced below about 50 percent by volume, the surface discharge rate is correspondingly reduced, making high speed cyclic or repeated imaging difficult or impossible.

In the second Middleton et al patent (U.S. Pat. No. 3,121,007) another type of photoconductor is considered, which includes a two phase photoconductive binder layer comprising photoconductive insulating matrix. The photoconductor is in the form a particulate photoconductive inorganic crystalline pigment broadly disclosed as being present in an amount from about 5 to 80 percent by weight. Here photo discharge is probably effected in a combination of charge carriers generated in the photoconductive insulating matrix material and charge carriers injected directly from the photoconductive crystalline pigment into the photoconductive insulating matrix.

U.S. Pat. No. 3,037,861 to Hoegl et al indicates that polyvinyl carbazole exhibits some long-wave U.V. sensitivity and suggests that spectral sensitivity can be extended into the visible light spectrum by the addition of dye sensitizers. This patent further suggests that other additives such as zinc oxide or titanium dioxide can be used in conjunction with polyvinyl carbazole as a photoconductor (with or without additive materials) to extend spectral sensitivity.

In addition to the above, certain specialized layered structures have been proposed for reflex imaging. In U.S. Pat. No. 3,165,405 to Hoesterey, for instance, there is a two layered zinc oxide binder structure. Hoesterey requires two separate contiguous photoconductive layers having different spectral sensitivities in order to carry out a particular reflex imaging sequence. This device utilizes the properties of multiple photoconductive layers in order to obtain the combined advantages of the separate photoresponse of the respective photoconductive layers.

Although the above patents rely upon distinct mechanisms of discharge throughout the photoconductive layer, they suffer from a common deficiency insofar as the photoconductive surface is very susceptible to abrasion, chemical attack, heat, and multiple exposures to light during cycling. As a result it is common to experience a gradual deterioration in the electrical characteristics of the photoconductive layer. This manifest, for instance, in printing of surface defects and scratches, and in the existence of localized areas of persistent conductivity.

Another form of composite photosensitive layer which has also been considered by the prior art includes a layer of photoconductive material which is covered with a relatively thick plastic layer and coated on a supporting substrate.

U.S. Pat. No. 3,041,166 to Bardeen describes such a configuration in which a transparent plastic material overlays a layer of vitreous selenium contained on a supporting substrate. The plastic material is described as one having a long range for charge carriers of the desired polarity. In operation, the free surface of the transparent plastic is electrostatically charged to a given polarity. The device is then exposed to activating radiation which generates a hole-electron pair in the photoconductive layer. The electron moves through the plastic layer and neutralizes a positive charge on the free surface of the plastic layer thereby creating an electrostatic image. Bardeen, however, does not teach any specific plastic materials which will function in this manner, and confines his examples to structures which use a photoconductor material for the top layer.

While the later patent represents a significant breakthrough, it has been found that it is very difficult, if not impossible to obtain and effectively utilize certain types of potentially suitable compounds as charge transmitting materials. This is true of various polycyclic aromatic subgroups, and particularly polycyclic aromatics, such as 1,2-benzanthracene and its derivatives which exhibit substantial π electron delocalization.

It is an object of the present invention to synthesize and utilize active polycyclic aromatic matrix components, particular vinyl polycyclic aromatic derivatives, suitable for transporting photoconductor-generated holes or electrons for general electrophotographic and xerographic purposes.

It is a further object to obtain new polymeric derivatives for use as active matrix components for xerographic purposes.

THE INVENTION

The above objects are realized by synthesizing and utilizing as active matrix material, inclusive of overcoating, an essentially polycyclic compound having at least 4 and preferably 4–6 cyclic nuclei, particularly, vinyl substituted polycyclics derived from a polycyclic aromatic reactant.

Such material is obtained in excellent yield by contacting a corresponding polycyclic reactant represented by the formula $$Q-H \qquad (I)$$

with at least a molar amount of a haloalkyl ether of the formula

$$(II)$$

in the presence of a catalytic amount of $SnCl_4$ or $TiCl_4$, wherein Q is defined as a substituted or unsubstituted polycyclic aromatic group having at least 4 fused ring nuclei and exhibiting substantial π electron delocalization. Of particular interest with respect to the present invention is the synthesis and use of polymers in which Q is defined as an aromatic polycyclic radical having 4–5 asymmetric aromatic nuclei and inclusive of a 1,2-benzanthracene group having substituents such as a lower alkyl (Ex. a 5-methyl-1,2-benzanthracene), a lower alkoxy or a phenyl substituted 1,2-benzantracene;

A in the above formulating agent is individually defined as an alkyl group such as an alkyl group of 1–8 carbon atoms and preferably a lower alkyl group of 1–8 carbon atoms such as methyl, isopropyl, or octyl;

For purposes of the present invention the molar ratio of formylating agent (formula II)-to-polycyclic reactant (formula I) can vary from about 1.0–1.5 to 1; a satisfactory catalytic amount of $SnCl_4$ and/or $TiCl_4$, for instance, is found to be in equimolar amount with respect to the haloalkyl ether formylating agent. This reaction step is usefully carried out, for instance, in methylene chloride at a temperature within the range of about −15° C to 40° C, and preferably at about 0° C–25° C, to obtain a decomposible intermediate product which, in turn, forms a polycyclic aldehyde intermediate represented by the formula

$$(III)$$

in excellent yield. The polycyclic aldehyde is then conveniently contaced with a reactive amount of a phosphine compound represented by the formulae

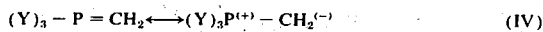

$$(IV)$$

wherein Y is conveniently defined as a phenyl or an alkyl group inclusive of phenyl, methyl and octadecyl, the reaction proceeding at about 20° C–85° C to obtain the corresponding vinyl-substituted polycyclic monomeric product represented by the formula $$Q - CH = CH_2 \qquad (V)$$

The vinyl monomeric product is converted, as desired, into the corresponding polymer by the use of a cationic mechanism. Such a polymeric reaction is conveniently effected by contacting the vinyl monomer in a reaction solvent with an initiating amount of a Lewis Acid such as Boron Trifluoride. This reaction is preferably effected in an inert atmosphere and in an essentially moisture-free environment. For this purpose the reaction solvent can be a chlorinated hydrocarbon such as methylene chloride or tetrahydrofurane. For most efficient polymerization, the temperature of the reaction mixture usefully varies from about −50° C to 75° C, depending upon the solvent used, and about 100–500 ppm of initiator is found sufficient to effect the reaction. The product is then conveniently recovered by precipitation with methanol and purified in the usual manner.

When a copolymer is desired, a controlled admixture of reactants containing up to 10% by weight of a second monomer such as a vinyl ether (ex. isobutylvinylether) or an acrylate is conveniently reacted at a temperature of about −50° C to 20° C and in the presence of a reaction solvent and catalyst of the types indicated above.

Suitable vinyl polycyclic aromatic monomers obtainable and usable in accordance with the present invention are reported, for instance, in Table I with respect to formula I–IV and some polymers exemplified in Table II.

The examples below are intended to illustrate various preferred embodiments of the instant invention.

EXAMPLE I (C-1)

About 0.1 mole of commercially obtained and chromatographically purified, 1,2 benzanthracene is dissolved in methylene chloride at about 0° C and admixed with about an equimolar amount of $SnCl_4$; 0.12 mole of α,α-dichloromethyl ether is then added slowly with continuous stirring for about 2 hours, the mixture being maintained at ambient temperature at least until HCl is no longer evolved. The resulting aldehyde intermediate product is then hydrolyzed and recovered. 0.5 Mole of the aldehyde is then contacted with exact equimolar amounts of Triphenylphosphine at about 0° C for 1 hour to obtain the vinyl monomeric product. This product is recovered and identified as 10-Vinyl-benzanthracene. The compound is reported in Table I as C-1.

EXAMPLE II (C-1)

Example I is repeated with the exception that the aldehyde is obtained by reaction with $HC(Cl)_2$-O-$C_{18}H_{37}$ as a formylating agent in place of α,α-dichloromethyl ether. The product is found to be identical with C-1.

EXAMPLE III (C-1)

The reaction of Example I is repeated with the exception that $TiCl_4$ is utilized as a catalyst to obtain the aldehyde. The resulting vinyl intermediate product is isolated, found to be identical with the product of Example I, and reported as C-I in Table I below.

EXAMPLE IV (C-5)

The reaction of Example I is repeated with the exception that the polycyclic aromatic reactant is 1-methyl-2,3-benzochrysene. The resulting 4-vinyl intermediate product is isolated and reported as C-5 in Table I below.

EXAMPLE VII (P-3)

The vinyl monomer identified as C-5 (Example IV) is reacted as in Example V but with an equivalent amount of $SbCl_3$ as an initiator to obtain the polymeric material identified as P-3 and reported in Table II below.

TABLE I

| Compound | Q | $\underset{CH-O-A}{\overset{Cl_2}{\|}}$ | Catalyst | Y |
|---|---|---|---|---|
| C-1 | 1,2-benzanthracene | HC—O—CH₃ / (Cl)₂ | SnCl₄ | ⌬— |
| C-1 | 1,2-benzanthracene | HC—O—C₁₈H₃₇ / (Cl)₂ | " | " |
| C-1 | 1,2-benzanthracene | HC—O—CH₁₁ / (Cl)₂ | " | CH₃— |
| C-1 | 1,2-benzanthracene | HC—O—CH₃ / (Cl)₂ | TiCl₄ | ⌬— |
| C-1 | 1,2-benzanthracene | HC—CH₂—O—C₃H₇ / (Cl)₂ | " | CH₃— |
| C-4 | 1,2,5,6-dibenzanthracene | HC—O—CH₃ / (Cl)₂ | SnCl₄ | ⌬— |
| C-4 | 1,2,5,6-dibenzanthracene | HC—O—CH₃ / (Cl)₂ | TiCl₄ | CH₃—⌬ |
| C-5 | 1-methyl-2,3-benzochrysene | HC—O—CH₃ / (Cl)₂ | SnCl₄ | ⌬— |
| C-5 | 1-2,3-methyl-benzochrysene | HC—O—CH₃ / (Cl)₂ | " | CH₃ |

EXAMPLE V (P-1)

0.01 Mole of the 10-vinylbenzanthracene obtained in Example I is dissolved in ethyl ether and then admixed with about 500 ppm of $BF_3$ with constant stirring at a temperature of about 0° C for about 3 hours. The resulting homopolymer is separated out and purified in the usual way, and cooled as HP-1 in Table II below.

EXAMPLE VI (P-2)

The polymerization reaction of Example V is repeated with the exception that the reaction is allowed to proceed in tetrahydrofuran at about 10° C for 4 hours. The resulting purified homopolymer is coded as HP-2 and reported in Table II below.

EXAMPLE VIII (CP-1)

Example V is repeated but with the addition of about 0.001 mole of isobutylvinyl ether to the 10-vinylbenzanthracene (C-1) reactant and the reaction allowed to proceed for about 6 hours at 0° C. The resulting copolymer, identified as CP-1 is isolated, purified and reported in Table II below.

TABLE II

| Polymer | Monomer | Comonomer | Solvent | Initiator | Reaction Temperature 0° | MW (Numerical) Average |
|---|---|---|---|---|---|---|
| HP- | C-1 (Ex 1) | — | CHCl₃ | BF₃ | 0° | 9,000 |
| HP-2 | C-1 | — | THF | " | 10° | 25,000 |
| HP-3 | C-5 | — | CHCl₃ | SbCl₃ | 10° | 15,000 |
| CP-1 | C-1 | isobutyl vinyl ether (.001 mole) | ETOEt | BF₃ | 0° | 40,000 |

EXAMPLE IX

Ten NESA glass plates identified respectively as S-1 through S-10 are coated on one side with a 0.5μ blocking layer of cured epoxy resin and a 0.5μ amorphous selenium photoconductive layer applied thereto in the usual way by vacuum condensation ($10^{-6}$ Torr).

A. To plates S-1 through S-5 there are applied overcoat layers of polymer P-1 (Example V) in layers of 10μ to about 30μ in thickness.

B. To the plates identified as S-6 through S-10 are applied overcoat layers varying from 10μ to about 30μ of polyvinyl pyrene having a numerical average molecular weight of about 10,000. The pyrene utilized is commercially obtained, purified and polymerized by acylation (ref. Vollman, Beeker, Corell and Streech; Justus Liebigs - Annalen Der Chemie: Vol. 531 (1937)).

The respective plates are thin corona charged at 900 volt, exposed to a monochromic light source at 4000 A at a plus of $2 \times 10^{12}$ photons/cm²/sec. and tested for electrical properties.* The results are reported in Table III below.

*P. Regensburger in "Optical Sensitization of Charge Carrier Transport in PVK", Photochemistry and Photobiology 8, p. 429–40 (November, 1968).

TABLE III*

| Sample | $\frac{dv}{dt} d^{-1}$ | $Eo \frac{v}{\mu}$ |
|---|---|---|
| S-1 | 1.30 | .54 |
| S-2 | 2.00 | .65 |
| S-3 | 3.60 | .90 |
| S-4 | 5.40 | 1.30 |
| S-5 | 10.0 | 2.00 |
| S-6 | .22 | .54 |
| S-7 | .42 | .65 |
| S-8 | .92 | .90 |
| S-9 | 1.60 | 1.30 |
| S-10 | 3.40 | 2.00 |

*900 volt.
$2 \times 10^{12}$ Photon/cm²/sec. flux
τ = 4000 A monochromic light

What is claimed is:

1. A process for producing a polymeric material from a polycyclic aromatic reactant of the formula:

Q — H wherein Q is defined as a polycyclic aromatic group having at least 4 fused ring nuclei; by contacting the reactant with at least a molar amount of a haloalkyl ether of the formula:

$$\underset{\underset{CH-O-A}{|}}{Cl_2}$$

wherein A is individually defined as an alkyl group; to obtain a corresponding polycyclic aldehyde intermediate represented by the formula:

$$\underset{Q-CH}{\overset{O}{\|}}$$

in the presence of a catalytic amount of $SnCl_4$ or $TiCl_4$; and then reacting the polycyclic aldehyde intermediate with a reactive amount of phosphine compound represented by the formulae:

$$(Y)_3 - P - CH_2 \longleftrightarrow (Y)_3P^{(+)} - CH_2^{(-)}$$

wherein Y is defined as a phenyl or an alkyl group; and contacting the resulting vinyl monomer in a reaction solvent with an initiating amount of a Lewis acid, this step being effected under vacuum in an essentially moisture-free environment.

2. The process of claim 1 wherein the haloalkyl ether intermediate is obtained in the presence of a catalytic amount of $SnCl_4$.

3. The process of claim 1 wherein the Lewis acid is $BF_3$.

4. The process of claim 1 wherein Q is a 1,2,5,6-dibenzanthracene.

5. The process of claim 1 wherein Q is a chrysene group.

6. The process of claim 1 wherein Q is a 2,3-benzochrysene group.

* * * * *